United States Patent
Tsim et al.

(10) Patent No.: US 7,455,862 B2
(45) Date of Patent: Nov. 25, 2008

(54) HERBAL COMPOSITIONS USEFUL IN CANCER TREATMENT

(75) Inventors: Wah Keung Karl Tsim, Hong Kong (CN); Xiao Yi Li, Hong Kong (CN)

(73) Assignee: Lee's Pharmaceutical (Hong Kong) Limited, Hong Kong (CN)

( * ) Notice: Subject to any disclaimer, the term of this patent is extended or adjusted under 35 U.S.C. 154(b) by 120 days.

(21) Appl. No.: 11/088,022

(22) Filed: Mar. 23, 2005

(65) Prior Publication Data

US 2006/0216366 A1    Sep. 28, 2006

(51) Int. Cl.
  *A61K 36/906* (2006.01)
  *A61K 36/00* (2006.01)

(52) U.S. Cl. ................... 424/756; 424/773; 424/777

(58) Field of Classification Search ................ None
  See application file for complete search history.

(56) References Cited

U.S. PATENT DOCUMENTS

| | | | |
|---|---|---|---|
| 6,190,875 B1 | 2/2001 | Ben-Artzi et al. | |
| 6,455,078 B1 * | 9/2002 | Wu | 424/725 |
| 2004/0105902 A1 * | 6/2004 | Chen | 424/756 |
| 2004/0234546 A1 * | 11/2004 | Lieberman | 424/195.18 |
| 2005/0020552 A1 * | 1/2005 | Aschkenasy et al. | 514/177 |
| 2005/0222258 A1 * | 10/2005 | Wang | 514/546 |

FOREIGN PATENT DOCUMENTS

CN    1184645 A  *  6/1998

OTHER PUBLICATIONS

Lee et al, In Vitro and In Vivo Antitumoral Phenanthrenes from the Aerial Parts of Dendrobium nobile, Planta Med. vol. 61, 1995, pp. 178-180.*

Bartlett et al., "Comparative analysis of the ability of leukocytes, endothelial cells and platelets to degrade the subendothelial basement membrane: evidence for cytokine dependence and detection of a novel sulfatase," *Immunol. Cell Biol.*, 73:113-124 (1995).

Liotta et al., "Tumor invasion and the extracellular matrix," *Lab. Invest.*, 49:636-649 (1983).

Nakajima et al., "Heparanases and tumor metastasis," *J. Cell. Biochem.*, 36:157-167 (1988).

Vlodavsky et al., "Expression of heparanase by platelets and circulating cells of the immune system: Possible involvement in diapedesis and extravasation," *Invasion & Metastasis*, 12:112-127 (1992).

Vlodavsky et al., "Involvement of heparanase in tumor metastasis and angiogenesis," *Is. J. Med.*, 24:464-470 (1988).

Vlodavsky et al., "Lymphoma cell mediated degradation of sulfated proteoglycans in the subendothelial extracellular matrix: Relationship to tumor cell metastasis," *Cancer Res.*, 43:2704-2711 (1983).

* cited by examiner

*Primary Examiner*—Christopher R Tate
*Assistant Examiner*—Deborah A. Davis
(74) *Attorney, Agent, or Firm*—K & L Gates LLP

(57) ABSTRACT

A herbal composition containing *Curcumae kwangsiensis* (Ezhu), *Herba Dendrobii nobile Lindl.* (Shihu), *Rhizoma Pinelliae preparatum* (Fabanxia), *Rhizoma Typhonii* (Baifuzi) and other optional herbs. The composition can be processed into a form for administering to human patients with a cancerous disease for improving their health.

16 Claims, 1 Drawing Sheet

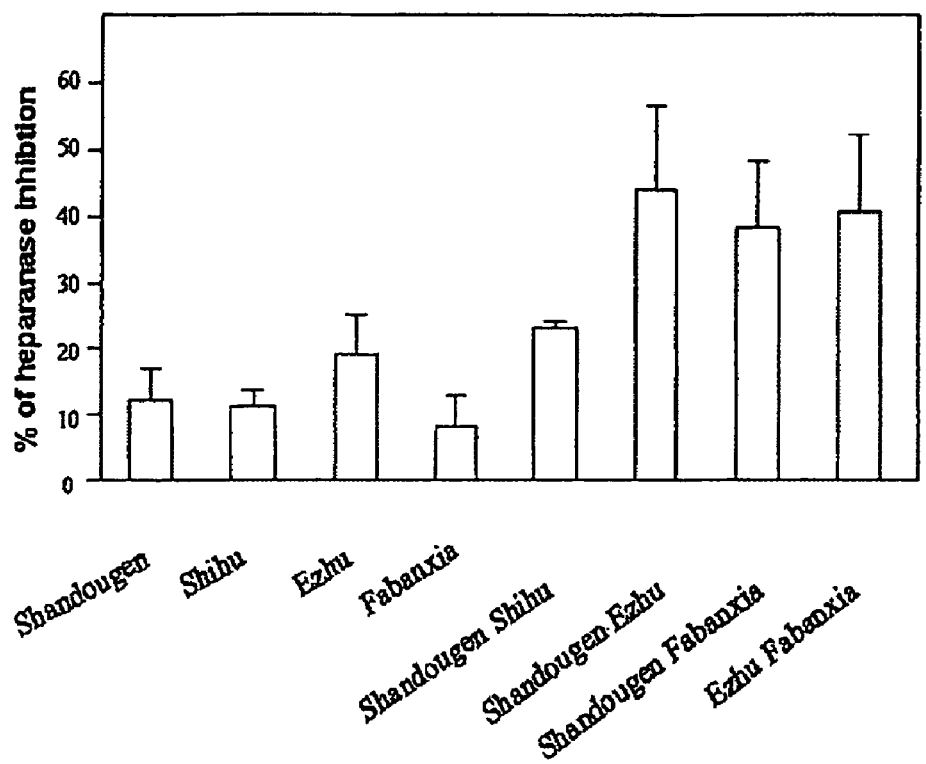

HERBAL COMPOSITIONS USEFUL IN CANCER TREATMENT

FIELD OF THE INVENTION

The present invention relates to compositions useful in cancer treatment. Particularly, the invention relates to compositions prepared from herbs commonly available for practicing Traditional Chinese Medicine and to methods of treating or improving cancerous conditions using the herbal compositions.

BACKGROUND OF THE INVENTION

Tumor cell invasion and secondary spread through the blood and lymphatic system, also known as metastasis, is the hallmark of malignant disease and the greatest challenge to cancer treatment. Tumor metastasis requires two important processes, namely, angiogenesis and tumor cell invasion of the basement membrane (BM) and the extracellular matrix (ECM). Circulating tumor cells arrested in the capillary beds of different organs must invade the endothelial cell lining and degrade its underlying basement membrane (BM) in order to escape into the extravascular tissue(s) where they establish metastasis (Liotta L. A. et al. (1983) Tumor invasion and the extracellular matrix, *Lab. Invest.*, 49:639-649).

Major components of the BM and the ECM are glycosaminoglycans, mainly heparan sulphate proteoglycan (HSPG). The basic HSPG structure includes a protein core and several linear heparan sulphate (HS) chains that covalently attached to the protein core. Several cellular enzymes (e.g., collagenase IV, plasminogen activator, cathepsin B, elastase) are thought to be involved in degradation of the BM (Liotta L. A. et al. (1983) Tumor invasion and the extracellular matrix, *Lab. Invest.*, 49:639-649). Among these enzymes is an endo-beta-D-glucuronidase (heparanase) that cleaves HS at specific intrachain sites, i.e., between GlcUA and GlcNAc sites (Vlodavsky I. et al. (1992) Expression of heparanase by platelets and circulating cells of the immune system: Possible involvement in diapedesis and extravasation, *Invasion & Metastasis*, 12:112-127; Nakajima M. et al. (1988) Heparanase and tumor metastasis *J. Cell. Biochem.*, 36:1 57-167; Vlodavsky I. et al. (1983) Lymphoma cell mediated degradation of sulphated proteoglycans in the subendothelial extracellular matrix: Relationship to tumor cell metastasis, *Cancer Res.*, 43:2704-2711; Vlodavsky I. et al. (1988) Involvement of heparanase in tumor metastasis and angiogenesis, *Is. J. Med.*, 24:464-470). Expression of an HS degrading heparanase was found to correlate with the metastatic potential at mouse lymphoma (Vlodavsky I. et al. (1983) Lymphoma cell mediated degradation of sulphated proteoglycans in the subendothelial extracellular matrix: Relationship to tumor cell metastasis, *Cancer Res.*, 43:2704-2711), fibrosarcoma and melanoma cells (Nakajima M. et al. (1988) Heparanase and tumor metastasis, *J. Cell. Biochem.*, 36:1 57-167). The same is true for human breast, bladder and prostate carcinoma cells (see U.S. Pat. No. 6,190,875). Moreover, elevated levels of heparanase were detected in sera (Nakajima M. et al. (1988) Heparanase and tumor metastasis, *J. Cell. Biochem.*, 36:157-167) and urine (U.S. Pat. No. 6,190,875) of metastatic tumor bearing animals and cancer patients and in tumor biopsies (Vlodavsky I. et al. (1988) Involvement of heparanase in tumor metastasis and angiogenesis, *Is. J. Med.*, 24:464-470). Heparanase has also been implicated in T cell-mediated delayed type hypersensitivity, experimental autoimmune encephalomyelities and adjuvant arthritis, suggesting that heparanase plays a role in cell diapedesis and extravasation associated with inflammation and autoimmune diseases.

Therefore, inhibitors of heparanase are useful for treating various cancers in human and other mammal subjects. An inhibitory effect on heparanase is a valuable biomarker in screening for substances as medicament in cancer treatment, which remains a serious challenges for the medical world.

SUMMARY OF THE INVENTION

The present invention provides novel compositions with inhibitory effects on heparanase, which are made from herbs commonly used in Traditional Chinese Medicine. The composition of the present invention are suitable for treating or improving pathological conditions involving elevated heparanase activities, such as tumor cell metastasis in various cancer patients.

In one aspect, the present invention provides an herbal composition comprising an effective amount of *Rhizoma Curcumae Kwangsiensis* (Ezhu), *Herba Dendrobium candidum* (Shihu), *Rhizoma Pinelliae preparatum* (Fabanxia), and *Rhizoma Typhonii* (Baifuzi). This composition may further comprise an effective amount of *Radix Sophora tonkinensis* (Shandougen), *Radix Arnebia euchroma* (Zicaogen), *Frutus lycium barbarum* (Gouqizi), *Radix Astagalus membranaceus* (Huangqi), *Herba Oldenlandia diffusa* (Baihuasheshecao), *Rhizoma polygonati* (Huangjing) and *Radix Glycyrrhizae* (Gancao). This herb mixture composition is processed according to the procedures known to people skilled in practicing herbal medicine, particularly, the Traditional Chinese Medicine. The processed composition may take any form as suitable, such as tea-like drinks (decoctions), pills, capsules, liquid alcoholic extracts, dried extracts, etc.

In another aspect, the present invention provides a composition comprising an effective amount of each extract of *Rhizoma Curcumae Kwangsiensis* (Ezhu), *Herba Dendrobium candidum* (Shihu), *Rhizoma Pinelliae preparatum* (Fabanxia), and *Rhizoma Typhonii* (Baifuzi). This extract mixture may further comprise an effective amount of each extract of *Radix Sophora tonkinensis* (Shandougen), *Radix Arnebia euchroma* (Zicaogen), *Frutus lycium barbarum* (Gouqizi), *Radix Astagalus membranaceus* (Huangqi), *Herba Oldenlandia diffusa* (Baihuasheshecao), *Rhizoma polygonati* (Huangjing) and *Radix Glycyrrhizae* (Gancao). In this aspect, the extract of each herbal ingredient is prepared separately and then mixed with the extracts of other herbs in a pre-prescribed ratio.

While each individual herb used in the present invention are commonly available and known among practitioners of Traditional Chinese Medicine, to the knowledge of the applicants, the composition with the particular ingredients disclosed herewith is unknown, much less its anticancer effects. Another aspect of the invention is that certain ingredients of the composition complementarily exert their medicinal effects with each other, creating synergy between them. For instance, synergistic effects for heparanase inhibition were obtained between *Rhizoma Curcumae kwangsiensis* (Ezhu) and *Radix Sophora tonkinensis* (Shandougen), between *Rhizoma Pinelliae preparatum* (Fabanxia) and *Radix Sophora tonkinensis* (Shandougen), and between *Rhizoma Curcumae kwangsiensis* (Ezhu) and *Rhizoma Pinelliae preparatum* (Fabanxia).

A better understanding of the present invention may be obtained in light of the following examples which are claimed to illustrate, but are not to be construed to limit the present invention.

BRIEF DESCRIPTION OF THE INVENTION

FIG. 1 shows the synergistic effect of heparanase inhibition between ingredients of the composition of the present invention.

DETAILED DESCRIPTION OF THE INVENTION

All the herbs used in the present invention are commercially available. After ascertaining the authenticity of the individual herbs, traditional methods may be used to process the composition of the present invention into a form suitable for administering to human subjects. Those conventional methods are known to people skilled in the art, described in books and commonly used by practitioners of herbal medicine. By way of example, not limitation, a suitable administering form can be tinctures, decoctions, or dry extracts. Extracts may be further process into pills, tablets, capsules or injections.

A tincture is prepared by suspending herbs in a solution of alcohol, such as, wine or liquor. After a period time of suspension, the liquid (the alcohol solution) may been administered two or three times a day, one teaspoon each time. A decoction is the most common form of herbal preparations. It is traditionally prepared in a clay pot, but nowadays it can also be prepared in glass, enamel or stainless steel containers. The herbs should be soaked for a period of time in a proper amount of water and then quickly brought to a boil and simmered until the amount of water is reduced by half.

An extract is a concentrated preparation of the essential constituents of the medicinal herb. Typically, the essential constituents are extracted from the herbs by suspending the herbs in an appropriate choice of solvent, typically, water, ethanol/water mixture, methanol, butanol, iso-butanol, acetone, hexane, petroleum ether or other organic solvents. The extracting process may be further facilitated by means of maceration, percolation, repercolation, counter-current extraction, turbo-extraction, or by carbon-dioxide hypercritical (temperature/pressure) extraction. After filtration to rid of herb debris, the extracting solution may be further evaporated and thus concentrated to yield a soft extract (extractum spissum) and/or eventually a dried extract, extracum siccum, by means of spray drying, vacuum oven drying, fluid-bed drying or freeze-drying. The soft extract or dried extract may be further dissolved in a suitable liquid to a desired concentration for administering or processed into a form such as pills, capsules, injections, etc.

As a particular embodiment of the present invention, a polysaccharide-enriched extract is prepared for each herbal ingredient. The extraction process is described below in detail.

Ten grams of an herb was cut into pieces and boiled 2 times sequentially with 5 volumes of water, 30 minutes each time. The soluble fraction (~50 ml) was filtered by filter paper and the filtrate was the total extract of the herb. Polysaccharide-enriched and non-polysaccharide-enriched extracts were prepared by the following protocol: Fifty milliliters (~50 ml) of the total extract were added to 3 volumes of 100% ethanol. The mixture was incubated at 4° C. overnight, and centrifuged at 3,000×g at 4° C. for 10 minutes. The supernatant was filtered and the filtered supernatant became the non-polysaccharide-enriched extract, whereas the pellet was the polysaccharide-enriched extract. All three extracts were concentrated by a Rotary evaporator Rotavapor® (Brinkmann, Westbury, N.Y.) and were dried to powder form with freeze-dryer. Appropriate concentration of each extract was obtained by dissolving the powder with an amount of water suitable for the heparanase activity assay.

The polysaccharide-enriched extracts were then tested for their abilities to inhibit heparanase. In order to determine anti-heparanase activity by the extract, a heparanase activity assay was carried out to determine the activity of a heparanase in the presence of the extract. The heparanase activity can be compared to a control, e.g., the activity of the same heparanase determined by the same activity assay but with the absence of the extract. In general, any suitable heparanase activity assay would allow determination of inhibitory effect on heparanase by an extract. There are many known assay protocols for determine heparanase activity. Although such assays are not part of the present invention, the following information is provided for easy reference.

A typical heparanase catalytic activity assay involves radiolabelling a substrate (either in vitro or metabolically) and analyzing the degraded products due to heparanase catalytic activity (Vlodavsky I. et al., (1992) Expression of heparanase by platelets and circulating cells of the immune system: Possible involvement in diapedesis and extravasation, *Invasion & Metastasis*, 12:112-127; Bartlett M. R. Underwood P. A. et al., (1995) Comparative analysis of the ability of leukocytes, endothelial cells and platelets to degrade the subendothelial basement membrane: evidence for cytokine dependence and detection of a novel sulfatase, *Immunol. Cell Biol.*, 73:113-124).

As part of the effort of searching effective herbal formulations for cancer treatment, a large number of herbs used in Traditional Chinese Medicine are studied for their anti-heparanase effect. For each herb, three types of preparations, namely, total extract (TE), polsaccharide-enriched extract (PER), non-polysaccharide-enriched extract (NPER), were made according to the process described in the foregoing. Table 1 summarizes the research data on 150 medicinal herbs.

TABLE 1

Effects of 150 Medicinal Herbs On Heparanase

| | Chinese Medicinal Herbs | Effects on Heparanase | | | | | |
|---|---|---|---|---|---|---|---|
| | | Heparanase-293T | | | Heparanase-placenta | | |
| | | TE | PER | NPER | TE | PER | NPER |
| 1 | *Rhizoma Curcumae kwangsiensis* (Ezhu) | +++ | −* | −* | +++ | + | + |
| 2 | *Herba Oldenlandia diffusa* (Baihuasheshecao) | − | − | − | −* | −* | −* |
| 3 | *Rhizoma Paris polyphylla* (Chonglou) | + | + | + | +++ | +++ | −* |
| 4 | *Radix Salvia miltiorrhizae* (Danshen) | − | −* | − | + | −* | − |
| 5 | *Rhizoma Sparganium stoloniferum* (Sanleng) | + | + | + | + | − | − |
| 6 | *Rhizoma Pinellia ternate* (Banxia) | − | − | − | + | − | −* |
| 7 | *Rhizoma Pinelliae preparatum* (Fabanxia) | + | + | + | ++ | + | − |

TABLE 1-continued

Effects of 150 Medicinal Herbs On Heparanase

|  | Chinese Medicinal Herbs | Heparanase-293T | | | Heparanase-placenta | | |
|---|---|---|---|---|---|---|---|
|  |  | TE | PER | NPER | TE | PER | NPER |
| 8 | *Herba Scutellariae barbatae* (Banhilian) | −* | −* | −* | − | − | − |
| 9 | *Pseudobulbus Cremastra appendiculata* (Shancigu) | −* | −* | −* | −* | −* | −* |
| 10 | *Lasiosphaera fenzlii/Calvatia gigantea* (Mabo) | −* | −* | −* | −* | − | − |
| 11 | *Ganoderma lucidum/G. sinense* (Lingzhi) | −* | −* | −* | −* | − | − |
| 12 | *Radix Angelicae sinensis* (Danggui) | −* | −* | −* | −* | ++ | ++ |
| 14 | *Danggui Buxue Tang* | −* | −* | −* | − | − | − |
| 15 | *Cordyceps sinensis* (Dongchongxiacao) | − | −* | −* | − | − | − |
| 16 | *Radix Astagalus membranaceus* (Huangqi) | − | − | − | −* | − | −* |
| 17 | *Radix Angelica pubescens* (Duhuo) | − | −* | − | − | − | −* |
| 18 | *Rhizoma Notopterygium incisum* (Qianghuo) | − | − | − | − | − | − |
| 19 | *Radix Angeliica dahurica* (Baizhi) | −* | −* | + | −* | −* | −* |
| 20 | *Rhizoma Ligusticam chuanxiong* (Chuanxiong) | −* | −* | − | − | −* | −* |
| 21 | *Peucedanum praeruptorum* (Qianhu) | +++ | −* | +++ | − | − | −* |
| 22 | *Radix Sophora tonkinensis* (Shandougen) | + | ++ | − | +++ | +++ | − |
| 23 | *Fructus Thichsanthes kirilowii* (Gualou) | − | −* | − | − | − | − |
| 24 | *Herba Taraxacum mongolicum* (Pugongying) | − | − | − | − | − | − |
| 25 | *Radix Sophora flavescens* (Kushen) | + | ++ | ++ | +++ | +++ | − |
| 26 | *Radix Arnebia euchroma* (Zicaogen) | − | − | ++ | ++ | + | + |
| 27 | *Semen Impatientis* (Jixingzi) | + | + | ++ | +++ | +++ | +++ |
| 28 | *Rhizoma Anemasshena asphodeloides Bge.* (Zhimu) | − | − | − | − | − | − |
| 29 | *Rhizoma Atractylodes lancea* (Sangzhu) | − | − | − | − | − | + |
| 30 | *Flemingia philippinensis* (Qianjinba) | −* | −* | −* | − | −* | +++ |
| 31 | *Caulis Polygoni multiflori* (Shouwuteng) | −* | −* | −* | +++ | −* | +++ |
| 32 | *Radix Curcuma wenyujin* (Yujin) | − | −* | − | −* | −* | −* |
| 33 | *Radix Ilex asprella* (Gangmeigen) | −* | −* | − | +++ | − | −* |
| 34 | *Polyporus umbellatus Fries* (Zhuling) | −* | −* | −* | + | −* | −* |
| 35 | *Poria cocos* (Fuling) | − | − | −* | − | − | −* |
| 36 | *Semen Arecae catechu L* (Binglang) | ++ | + | − | − | − | −* |
| 37 | *Furctus Rosa laevigata Michx* (Jinyingzi) | − | − | − | − | − | −* |
| 38 | *Rhizoma Cyperus rotundus* (Xiangfu) | − | − | − | −* | − | −* |
| 39 | *Fructus Chaenomeles sinensis* (Nanmugua) | ++ | − | − | −* | −* | −* |
| 40 | *Fructus Aurantii* (Zhishi) | − | ++ | − | − | − | + |
| 41 | *Rhizoma Arisaematis* (Tiannanxing) | ++ | ++ | + | −* | − | −* |
| 42 | *Bombyx mori Linnaeus* (Cansha) | −* | ++ | − | −* | − | −* |
| 43 | *Fructus Forsythia suspense* (Lianqiao) | − | − | −* | + | − | − |
| 44 | *Radix Aconiti kusnezoffii* (Caowu) | − | − | − | +++ | − | − |
| 45 | *Herba Dianthus superbus* (Qumai) | − | − | − | −* | −* | −* |
| 46 | *Rhizoma Dryopteris crassirhizoma* (Guanzhong) | − | −* | ++ | − | + | −* |
| 47 | *Flos Lonicerae* (Jinyinhua) | − | − | −* | − | − | −* |
| 48 | *Flos Serratum chinensis* (Mumian) | − | − | − | + | − | −* |
| 49 | *Herba Polycapaea corymbesa* (Baiguding) | − | − | +++ | − | − | + |
| 50 | *Herba Gerbera piloselloides* (Maodading) | ++ | ++ | + | + | + | +++ |
| 51 | *Rhizoma Belamcanda chinensis* (Shengan) | +++ | + | − | ++ | +++ | +++ |
| 52 | *Caulis Psychotria serpens* | ++ | − | + | ++ | +++ | + |
| 53 | *Rhizoma Cynanchum stauntonii* (Baiqian) | +++ | − | ++ | +++ | − | −* |
| 54 | *Rhizoma Costus speciosus* (Biqiaojiang) | −* | −* | −* | +++ | − | −* |
| 55 | *Radix Aristolochia westlandi* (Guangfangji) | −* | −* | − | −* | −* | −* |
| 56 | *Radix Isatidis indigotica* (Banlangen) | − | − | − | −* | − | − |
| 57 | *Rhizoma Typhonii* (Baifuzi) | + | −* | + | ++ | −* | − |
| 58 | *Radix Aconiti lateralis preparata* (Chuanwu) | −* | −* | − | − | − | − |
| 59 | *Flolium isatidis indigotica* (Daqingye) | ++ | ++ | ++ | + | − | − |
| 60 | *Herba Lycopus lucidus* (Zelan) | − | ++ | ++ | + | ++ | −* |
| 61 | *Herba Pistia stratiotes* (Daipiao) | − | ++ | ++ | − | −* | − |
| 62 | *Semen Caesalpinia minax* (Huijiayunshi) | ++ | − | ++ | +++ | − | + |
| 63 | *Ficus pumila* (Xueli) | − | −* | + | − | +++ | +++ |
| 64 | *Folium Podocarpus Macrophylla* (Xiaoluohansong) | −* | −* | −* | +++ | −* | − |
| 65 | *Caulis Oldenlandia hedytidea* (Niubaiteng) | +++ | +++ | +++ | ++ | −* | + |
| 66 | *Rhizoma Bombyx mori Linnaeus* (Sutiejue) | −* | −* | −* | + | − | − |
| 67 | *Herba Asarum Maxinum* (Dahuaxixin) | −* | +++ | +++ | − | − | − |
| 68 | *Rhizoma Coptis Chinensis* (Huanglian) | −* | − | −* | −* | − | −* |
| 69 | *Fructus Evodia rutaecarpa* (Wuzhuyu) | −* | −* | −* | ++ | − | − |
| 70 | *Herba Dendrobium candidum* (Shihu) | − | − | − | ++ | − | + |
| 71 | *Frutus lycium barbarum* (Gouqizi) | − | −* | − | ++ | − | − |
| 72 | *Herba Nerrilia, Nervilia fordii* (Qingtiankui) | + | −* | + | + | − | −* |
| 73 | *Rhizoma Cordydalis yanhusuo* (Yanhusuo) | + | + | ++ | + | − | ++ |
| 74 | *Herba Dendrobii nobile Lindl.* (Shihu) | +++ | ++ | + | +++ | ++ | + |
| 75 | *Radix Cordonpsis pilosulae* (Dangshen) | ++ | ++ | ++ | + | − | + |
| 76 | *Bulbus Fritillaria puqiensis* (Beimu) | + | + | +++ | ++ | ++ | ++ |

TABLE 1-continued

Effects of 150 Medicinal Herbs On Heparanase

| | Effects on Heparanase | | | | | |
|---|---|---|---|---|---|---|
| | Heparanase-293T | | | Heparanase-placenta | | |
| Chinese Medicinal Herbs | TE | PER | NPER | TE | PER | NPER |
| 77 Bulus Fritilaria anhuiengis (Beimu) | + | − | ++ | − | − | + |
| 78 Syngnathus (Hujiao) | + | − | − | ++ | + | − |
| 79 Synagnathus hardwickii (Hailong) | ++ | − | − | −* | + | − |
| 80 Radix Panacis quinquefolii (Xiyangshen) | − | − | − | − | − | − |
| 81 Hippocampus kuda (Dahaima) | − | − | − | − | + | − |
| 82 Radix Ramax ginseng (Renshen) | − | − | − | −* | − | − |
| 83 Panax Quinquefolium (Huaqishen) | − | − | − | + | − | − |
| 84 Fritillaria ussunensis (Pingbeimu) | − | − | − | − | −* | − |
| 85 Fritillaria taipaiensis (Taibaibeimu) | − | −* | −* | − | − | − |
| 86 Fritillaria thanbergii (Zhebeimu) | − | −* | −* | − | − | − |
| 87 Semen Ziziphi Spinosae (Suanzaoren) | − | ++ | − | −* | −* | −* |
| 88 Semen Alpiniae katsumada (Caodoukou) | − | + | + | − | − | − |
| 89 Rhizoma Curcumae longae (Jianghuang) | − | − | + | − | − | − |
| 90 Radix et Rhizoma rhei (Dahuang) | + | + | ++ | − | − | ++ |
| 91 Flos Magnoliae officinalis (Houpu) | −* | − | − | −* | + | + |
| 92 Semen Nelumbo nucifera (Lianzixin) | ++ | +++ | +++ | +++ | +++ | +++ |
| 93 Radix Solena amplexicaulis (Maogua) | − | +++ | +++ | −* | +++ | ++ |
| 94 Herba Leonurus heterophyllus (Yimucao) | − | − | − | + | + | − |
| 95 Pheretimea aspergillum (Dilong) | − | − | − | − | − | − |
| 96 Semen Euphorbia lathyris (Qianjinzi) | − | + | + | − | − | − |
| 97 Radix Euphorbia kansui (Gansui) | − | − | − | − | − | − |
| 98 Hirude nipponica (Shuizhi) | − | − | − | −* | −* | −* |
| 99 Semen Croton tiglium (Badou) | − | − | −* | ++ | +++ | −* |
| 100 Semen Strychnos nux-vomica (Muqianzi) | −* | −* | −* | −* | − | −* |
| 101 Radix Morinda officinalis (Bajitian) | − | + | − | −* | − | −* |
| 102 Radix Aconitum brachypodum (Xueshangyizhihao) | −* | −* | − | −* | −* | − |
| 103 Flos Datula metel (Yangjinhua) | − | ++ | + | − | + | + |
| 104 Mylabris (Banmao) | − | − | − | − | − | − |
| 105 Semen Dioscorea bulbifera (Huangyaozi) | −* | − | + | + | +++ | + |
| 106 Flos Carthamus tinctorius (Honghua) | −* | −* | + | −* | −* | ++ |
| 107 Flos Prunella vulgaris (Xiakucao) | − | − | − | − | ++ | + |
| 108 Eupolyphaga seu Steleophaga (Tubiechong) | −* | −* | −* | −* | − | −* |
| 109 Rhizoma Paris polyphylla (Zaoxiu) | − | + | +++ | + | −* | + |
| 110 Semen Ligustrum Lucidum (Nuzhenzi) | + | − | + | −* | −* | −* |
| 111 Radix Notoginseng (Sanqi) | − | − | − | −* | − | − |
| 112 Semen Coix lacryma-jobi (Yiyiren) | − | − | − | − | − | − |
| 113 Radix Stemona sessilifolia (Baibu) | + | + | ++ | − | − | − |
| 114 Semen Prunus humilis (Yuliren) | − | − | ++ | − | − | − |
| 115 Pollen Typha angustifolia (Puhuang) | +++ | − | − | − | − | − |
| 116 Schelfflera octophylla (Yajiaomu) | ++ | − | − | − | − | − |
| 117 Rhizoma Anemones raddeana Regel (Liangmianzhen) | −* | − | − | − | − | − |
| 118 Flos chrysanthemi (Juhua) | − | − | − | −* | − | −* |
| 119 Rhizoma polygonati (Huangjing) | − | − | − | +++ | − | − |
| 120 Radix rehmanniae (Dihuang) | − | − | + | − | − | − |
| 121 Rhizoma Polygonati odorati (Yuzhu) | + | + | − | − | − | − |
| 122 Semen nelumbinis (Lianzi) | − | − | − | − | − | − |
| 123 Radix paeoniae alba (Baishao) | − | − | − | − | − | −* |
| 124 Radix paeoniae rubra (Chishao) | − | − | + | − | − | −* |
| 125 Caulis polygoni multiflori (Heshouwu) | − | − | + | − | − | − |
| 126 Herba epimedii (Yinyanghuo) | − | − | − | − | − | −* |
| 127 Rhizoma Pseudodrynaria coronans (Gusuibu) | − | − | − | − | − | −* |
| 128 Rhizoma cimicifugae (Shengma) | −* | − | − | − | − | − |
| 129 Caulis Sargentodoxa cuneata (Daxueteng) | − | − | − | − | − | − |
| 130 Piper kadsura (Haifengteng) | − | −* | − | − | − | − |
| 131 Luffae Fructus Retunervus (Guangzhousigua) | −* | − | − | +++ | ++ | − |
| 132 Flos Magolia coco (Yehehuan) | −* | − | −* | − | − | − |
| 133 Herba Gentiana Loureiri (Huananlongdan) | −* | − | − | − | +++ | − |
| 134 Torilis japonica (Yaoyi) | − | − | − | −* | +++ | − |
| 135 Herba Anisomeles indica (Fangfengcao) | −* | − | − | −* | −* | − |
| 136 Herba Thalspi arvense (Xinming) | − | − | − | − | − | − |
| 137 Flos Anisopappus chinensis (Shanhuangju) | ++ | + | ++ | ++ | − | − |
| 138 Flos Artemisia lactiflora (Sijicai) | −* | −* | + | −* | −* | − |
| 139 Herba Eupatoium fortunei (Peilan) | − | + | − | − | ++ | − |
| 140 Herba Equisetum debile (Weiguancao) | − | + | −* | − | − | −* |
| 141 Rhizoma Alocasia macrorrhiza (Haiyu) | −* | ++ | − | − | + | − |
| 142 Rhizoma Clematis chinensis (Jinmaogouji) | −* | −* | −* | −* | −* | −* |
| 143 Sargassum fusiforme (Haizao) | − | − | − | − | − | − |
| 144 Thallus eckloniae (Kunbu) | − | − | − | − | − | − |
| 145 Radix Scutellariae barcalensis (Huangqi) | − | + | − | + | − | − |

TABLE 1-continued

Effects of 150 Medicinal Herbs On Heparanase

| | | Effects on Heparanase | | | | |
| | | Heparanase-293T | | | Heparanase-placenta | | |
| | Chinese Medicinal Herbs | TE | PER | NPER | TE | PER | NPER |
|---|---|---|---|---|---|---|---|
| 146 | *Radix Rehmamnia glutinosa* (Shengdi) | − | − | − | − | − | − |
| 147 | *Desmodium Styracifolium* (Jinqiancao) | − | − | − | − | − | − |
| 148 | *Cortex moutan* (Danpi) | − | − | − | − | − | − |
| 149 | *Flos Inula japonica* (Xuanfuhua) | − | − | − | − | − | − |
| 150 | *Radix Clematis chinensis* (Weilingxian) | −* | −* | −* | −* | −* | −* |

Notes:
1. TE: total extract; PER: polysaccharide-enriched extract; NPER: non-polysaccharide enriched extract
2. "−": 1-25% inhibition, "+": 26-50% inhibiton, "++": 51-75% inhibition, "+++": 76-100% inhibition, "−*": activation In addition to the above study on individual herbs, synergistic effects between two individual herbs when used in combination were also examined. As shown in FIG. 1, the ingredients of the composition of the present invention demonstrate a synergic effect in terms of their inhibitory action on heparanase. For example, the sum of heparanase inhibition by *Rhizoma Curcumae kwangsiensis* (Ezhu) and *Radix Sophora tonkinensis* (Shandougen) acting individually was about 32.5% while it was 44.5% when used in combination. For *Rhizoma Pinelliae preparatum* (Fabanxia) and *Radix Sophora tonkinensis* (Shandougen), it was 21% verses 38.5%. For *Rhizoma Curcumae kwangsiensis* (Ezhu) and *Rhizoma Pinelliae preparatum* (Fabanxia), it was 28.5% verses 40.5%. The synergy was significant. In FIG. 1, the Chinese characters indicate the each herb's name in Chinese.

As a particular embodiment of the present invention, an anti-cancer herbal composition is provided herewith as an example. This composition contains the following ingredients: *Rhizoma Curcumae kwangsiensis* (Ezhu), *Herba Dendrobii nobile Lindl.* (Shihu), *Rhizoma Pinelliae preparatum* (Fabanxia), *Rhizoma Typhonii* (Baifuzi), *Radix Sophora tonkinensis* (Shandougen), *Radix Arnebia euchroma* (Zicaogen), *Frutus lycium barbarum* (Gouqizi), *Radix Astagalus membranaceus* (Huangqi), *Herba Oldenlandia diffusa* (Baihuasheshecao), *Rhizoma polygonati* (Huangjing) and *Radix Glycyrrhizae* (Gancao).

Among them, *Rhizoma Curcumae kwangsiensis* (Ezhu), *Herba Dendrobii nobile Lindl.* (Shihu), *Rhizoma Pinelliae preparatum* (Fabanxia), *Rhizoma Typhonii* (Baifuzi) are essential ingredients and must be included in the composition, while the remaining listed herbs are optional, one or more of which may be omitted from the composition. An effective amount of each herb is used in the composition. The term "effective amount" means the amount of herbal ingredient will contribute towards the overall composition's ability to provide the intended effect. The effective amount of each herb can be determined by people skilled in the art. The following dosage ranges (for a single dose) are provided for easy reference or guidance. Dosages outside the described ranges may also be effective and provide satisfactory results.

*Rhizoma Curcumae kwangsiensis* (Ezhu): 5-50 grams, preferably about 15 grams;

*Herba Dendrobii nobile Lindl.* (Shihu): 5-50 grams, preferably about 10 grams;

*Rhizoma Pinelliae preparatum* (Fabanxia): 5-20 grams, preferably about 10 grams;

*Rhizoma Typhonii* (Baifuzi): 5-20 grams, preferably about 10 grams;

*Radix Sophora tonkinensis* (Shandougen): 5-20 grams, preferably about 10 grams;

*Radix Arnebia euchroma* (Zicaogen): 5-30 grams, preferably about 10 grams;

*Frutus lycium barbarum* (Gouqizi): 10-30 grams, preferably about 10 grams;

*Radix Astagalus membranaceus* (Huangqi): 10-30 grams, preferably about 15 grams;

*Herba Oldenlandia diffuse* (Baihuasheshecao): 20-40 grams, preferably about 30 grams;

*Rhizoma polygonati* (Huangjing): 20-50 grams, preferably about 30 grams;

*Radix Glycyrrhizae* (Gancao): 5-20 grams, preferably about 5 grams;

As discussed in the above, by conventional or known methods to people skilled in the art, the herbal composition is further processed into one of the suitable forms for human consumption as a measure of treatment or prevention of cancers. The herbal ingredients of the composition may be mixed before being further processed. Or, each ingredient is processed individually first and then the resulting processed ingredients, such as, for example, total extracts or polysaccharide-enriched extracts of each herb, are mixed according to the specified relative amounts. For example, if the amount of the total extract made from 5-50 grams of *Rhizoma Curcumae kwangsiensis* (Ezhu) is used in the composition, the amount of the total extract made from 5-20 grams of *Rhizoma Pinelliae preparatum* (Fabanxia) should be used to keep their relative amounts consistent with the above prescribed ranges.

Another particular embodiment of the present invention is defined by the relative amounts of its ingredients. It contains *Rhizoma Curcumae kwangsiensis* (Ezhu), *Herba Dendrobii nobile Lindl.* (Shihu), *Rhizoma Pinelliae preparatum* (Fabanxia), *Rhizoma Typhonii* (Baifuzi), where the ratio between *Curcumae kwangsiensis* (Ezhu) and *Herba Dendrobii nobile Lindl.* (Shihu) is from 0.1 to 10 by weight; the ratio between *Curcumae kwangsiensis* (Ezhu) and *Rhizoma Pinelliae preparatum* (Fabanxia) is from 0.25 to 10 by weight; the ratio between *Curcumae kwangsiensis* (Ezhu) and *Rhizoma Typhonii* (Baifuzi) is from 0.25 to 10 by weight. Preferably, the above ratios are 0.5-5, 1.0-5.0, and 1.0-5.0, respectively. More preferably, the above ratios are 1.5, 1.5, and 1.5, respectively. The ratio of weight is determined before the herbs are processed.

The above composition may optionally further comprise one or more herbs selected from the group consisting *Radix Sophora tonkinensis* (Shandougen), *Radix Arnebia euchroma* (Zicaogen), *Frutus lycium barbarum* (Gouqizi), *Radix Asta-*

*galus membranaceus* (Huangqi), *Herba Oldenlandia diffusa* (Baihuasheshecao), *Rhizoma polygonati* (Huangjing) and *Radix Glycyrrhizae* (Gancao). When one or more optional herbs are present in the composition, the ratios (by weight) between *Curcumae kwangsiensis* (Ezhu) and the optional herbs are 0.25-10, 0.16-10, 0.16-5.0, 0.16-5.0, 0.125-2.5, 0.1-2.5, and 0.25-10, respectively. Preferably, the ratios are 0.5-5, 0.3-5, 0.3-2.5, 0.3-2.5, 0.25-1, 0.2-1 and 0.5-5, respectively. More preferably, the ratios are 1.5, 1.5, 1.5, 1, 0.5, 0.5, and 3 respectively. The ratio of weight is determined before the herbs are processed.

While there have been described and pointed out fundamental novel features of the invention as applied to a preferred embodiment thereof, it will be understood that various omissions and substitutions and changes, in the form and details of the packages and methods illustrated, may be made by those skilled in the art without departing from the spirit of the invention. For example, it is expressly intended that all combinations of those elements and/or method steps which perform substantially the same function in substantially the same way to achieve the same results are within the scope of the invention.

The invention is not limited by the embodiments described above which are presented as examples only but can be modified in various ways within the scope of protection defined by the appended patent claims.

What is claimed is:

1. An anti-heparanase composition, comprising:
an effective amount of *Curcumae kwangsiensis* (Ezhu);
an effective amount of *Herba Dendrobii nobile Lindl.* (Shihu);
an effective amount of *Rhizoma Pinelliae preparatum* (Fabanxia); and
an effective amount of *Rhizoma Typhonii* (Baifuzi);
wherein the ratio by weight between *Curcumae kwangsiensis* (Ezhu) and *Herba Dendrobii nobile Lindl.* (Shihu) is 0.1-10;
the ratio by weight between *Curcumae kwangsiensis* (Ezhu) and *Rhizoma Pinelliae preparatum* (Fabanxia) is 0.25-10; and
the ratio by weight between *Curcumae kwangsiensis* (Ezhu) and *Rhizoma Typhonii* (Baifuzi) is 0.25-10.

2. The composition of claim 1, further comprising:
an effective amount of *Radix Sophora tonkinensis* (Shandougen);
an effective amount of *Radix Arnebia euchroma* (Zicaogen);
an effective amount of *Frutus lycium barbarum* (Gouqizi);
an effective amount of *Radix Astagalus membranaceus* (Huangqi); and
an effective amount of *Oldenlandia diffusa* (Baihuasheshecao).

3. The composition of claim 2, further comprising:
an effective amount of *Rhizoma polygonati* (Huangjing); and
an effective amount of *Radix Glycyrrhizae* (Gancao).

4. An anti-heparanase composition, comprising:
an effective amount of *Curcumae kwangsiensis* (Ezhu) extract;
an effective amount of *Herba Dendrobii nobile Lindl.* (Shihu) extract;
an effective amount of *Rhizoma Pinelliae preparatum* (Fabanxia) extract; and
an effective amount of *Rhizoma Typhonii* (Baifuzi) extract;
said extract being a total extract, polysaccharide-enriched extract, or non-polysaccharide-enriched extract, and
wherein prior to extracting the ratio by weight between *Curcumae kwangsiensis* (Ezhu) and *Herba Dendrobii nobile Lindl.* (Shihu) is 0.1-10;
the ratio by weight between *Curcumae kwangsiensis* (Ezhu) and *Rhizoma Pinelliae preparatum* (Fabanxia) is 0.25-10; and
the ratio by weight between *Curcumae kwangsiensis* (Ezhu) and *Rhizoma Typhonii* (Baifuzi) is 0.25-10.

5. The composition of claim 4, further comprising:
an effective amount of *Radix Sophora tonkinensis* (Shandougen) extract;
an effective amount of *Radix Arnebia euchroma* (Zicaogen) extract;
an effective amount of *Frutus lycium barbarum* (Gouqizi) extract;
an effective amount of *Radix Astagalus membranaceus* (Huangqi) extract; and
an effective amount of *Oldenlandia diffusa* (Baihuasheshecao) extract.

6. The composition of claim 5, further comprising:
an effective amount of *Rhizoma polygonati* (Huangjing) extract; and
an effective amount of *Radix Glycyrrhizae* (Gancao) extract.

7. The composition of claim 2, wherein:
the ratio by weight between *Curcumae kwangsiensis* (Ezhu) and *Radix Sophora tonkinensis* (Shandougen) is 0.25-10;
the ratio by weight between *Curcumae kwangsiensis* (Ezhu) and *Radix Arnebia euchroma* (Zicaogen) is 0.16-10;
the ratio by weight between *Curcumae kwangsiensis* (Ezhu) and *Frutus lycium barbarum* (Gouqizi) is 0.16-5;
the ratio by weight between *Curcumae kwangsiensis* (Ezhu) and *Radix Astagalus membranaceus* (Huangqi) is 0.16-5; and
the ratio by weight between *Curcumae kwangsiensis* (Ezhu) and *Oldenlandia diffusa* (Baihuasheshecao) is 0.125-2.5.

8. The composition of claim 3, wherein:
the ratio by weight between *Curcumae kwangsiensis* (Ezhu) and *Rhizoma polygonati* (Huangjing) is 0.1-2.5; and
the ratio by weight between *Curcumae kwangsiensis* (Ezhu) and *Radix Glycyrrhizae* (Gancao) is 0.25-10.

9. The composition of claim 1, wherein:
the ratio by weight between *Curcumae kwangsiensis* (Ezhu) and *Herba Dendrobii nobile Lindl.* (Shihu) is 0.5-5;
the ratio by weight between *Curcumae kwangsiensis* (Ezhu) and *Rhizoma Pinelliae preparatum* (Fabanxia) is 1-5; and
the ratio by weight between *Curcumae kwangsiensis* (Ezhu) and *Rhizoma Typhonii* (Baiftizi) is 1-5.

10. The composition of claim 7, wherein:
the ratio by weight between *Curcumae kwangsiensis* (Ezhu) and *Radix Sophora tonkinensis* (Shandougen) is 0.5-5;
the ratio by weight between *Curcumae kwangsiensis* (Ezhu) and *Radix Arnebia euchroma* (Zicaogen) is 0.3-5;
the ratio by weight between *Curcumae kwangsiensis* (Ezhu) and *Frutus lycium barbarum* (Gouqizi) is 0.3-2.5;
the ratio by weight between *Curcumae kwangsiensis* (Ezhu) and *Radix Astagalus membranaceus* (Huangqi) is 0.3-2.5; and the ratio by weight between *Curcumae kwangsiensis* (Ezhu) and *Oldenlandia diffusa* (Baihuasheshecao) is 0.25-1.

11. The composition of claim 8, wherein:

the ratio by weight between *Curcumae kwangsiensis* (Ezhu) and *Rhizoma polygonati* (Huangjing) is 0.2-1; and the ratio by weight between *Curcumae kwangsiensis* (Ezhu) and *Radix Glycyrrhizae* (Gancao) is 0.5-5.

12. The composition of claim 5, wherein prior to extracting:

the ratio by weight between *Curcumae kwangsiensis* (Ezhu) and *Radix Sophora tonkinensis* (Shandougen) is 0.25-10;

the ratio by weight between *Curcumae kwangsiensis* (Ezhu) and *Radix Arnebia euchroma* (Zicaogen) is 0.16-10;

the ratio by weight between *Curcumae kwangsiensis* (Ezhu) and *Frutus lycium barbarum* (Gouqizi) is 0.16-5;

the ratio by weight between *Curcumae kwangsiensis* (Ezhu) and *Radix Astagalus membranaceus* (Huangqi) is 0.16-5; and the ratio by weight between *Curcumae kwangsiensis* (Ezhu) and *Oldenlandia diffusa* (Baihuasheshecao) is 0.125-2.5.

13. The composition of claim 6, wherein prior to extracting:

the ratio by weight between *Curcumae kwangsiensis* (Ezhu) and *Rhizoma polygonati* (Huangjing) is 0.1-2.5; and the ratio by weight between *Curcumae kwangsiensis* (Ezhu) and *Radix Glycyrrhizae* (Gancao) is 0.25-10.

14. The composition of claim 4, wherein prior to extracting:

the ratio by weight between *Curcumae kwangsiensis* (Ezhu) and *Herba Dendrobii nobile Lindl.* (Shihu) is 0.5-5;

the ratio by weight between *Curcumae kwangsiensis* (Ezhu) and *Rhizoma Pinelliae preparatum* (Fabanxia) is 1-5; and the ratio by weight between *Curcumae kwangsiensis* (Ezhu) and *Rhizoma Typhonii* (Baifuzi) is 1-5; said extract being a total extract, polysaccharide-enriched extract, or non-polysaccharide-enriched extract.

15. The composition of claim 12, wherein prior to extracting:

the ratio by weight between *Curcumae kwangsiensis* (Ezhu) and *Radix Sophora tonkinensis* (Shandougen) is 0.5-5;

the ratio by weight between *Curcumae kwangsiensis* (Ezhu) and *Radix Arnebia euchroma* (Zicaogen) is 0.3-5;

the ratio by weight between *Curcumae kwangsiensis* (Ezhu) and *Frutus lycium barbarum* (Gouqizi) is 0.3-2.5;

the ratio by weight between *Curcumae kwangsiensis* (Ezhu) and *Radix Astagalus membranaceus* (Huangqi) is 0.3-2.5; and the ratio by weight between Curcumae kwangsiensis (Ezhu) and *Oldenlandia diffusa* (Baihuasheshecao) is 0.25-1; said extract being a total extract, polysaccharide-enriched extract, or non-polysaccharide-enriched extract.

16. The composition of claim 13, wherein prior to extracting:

the ratio by weight between *Curcumae kwangsiensis* (Ezhu) and *Rhizoma polygonati* (Huangjing) is 0.2-1; and the ratio by weight between *Curcumae kwangsiensis* (Ezhu) and *Radix Glycyrrhizae* (Gancao) is 0.5-5; said extract being a total extract, polysaccharide-enriched extract, or non-polysaccharide-enriched extract.

\* \* \* \* \*